United States Patent [19]

Sweger

[11] 3,932,602
[45] Jan. 13, 1976

[54] NON-STINGING WOUND DRESSING

[75] Inventor: Ulf Alan Sweger, Marbella, Spain

[73] Assignee: Novitas Nuprot SA, Freibourg, Switzerland

[22] Filed: Dec. 13, 1973

[21] Appl. No.: 424,422

[30] Foreign Application Priority Data
Dec. 27, 1972 Switzerland.................. 16962/72

[52] U.S. Cl. ............................................. 424/45
[51] Int. Cl.² ........................................ A61L 9/04
[58] Field of Search ............ 424/43, 44, 45, 30

[56] References Cited
UNITED STATES PATENTS

| | | |
|---|---|---|
| 2,972,545 | 2/1961 | Briskin................................ 424/45 |
| 3,269,903 | 8/1966 | Von Fieandt et al................ 424/45 |
| 3,476,853 | 11/1969 | Jatul et al. ........................... 424/45 |
| 3,577,516 | 5/1971 | Gould et al. ......................... 424/45 |

Primary Examiner—Stanley J. Friedman
Attorney, Agent, or Firm—Elliot N. Schubert; John J. McDonnell

[57] ABSTRACT

This invention is concerned with a non-stinging wound dressing. This wound dressing is characterized by plastics dissolved in a solvent system of stinging and non-stinging solvent, the combination of which provides a non-stinging solvent system with sufficient polarity to dissolve the plastic. This wound dressing is preferably applied to wounds as an aerosol spray dressing containing bacteriostatic agents.

3 Claims, No Drawings

NON-STINGING WOUND DRESSING

The present invention is concerned with a clean, convenient, economical and effective wound dressing for small wounds, abrasions, burns, and varicose and decubitus ulcers. Conventional gauze bandages and plasters do not protect wounds from infection and water, and must be changed often. Thus, these conventional wound coverings often interfere with healing, inhibit normal bathing of the area around the wound, and are uneconomical in terms of staff time required for changing. Wound dressings of plastics in solvents avoid many of the problems associated with conventional dressings in that they protect a wound against infection, permit visual inspection of wound healing, allow the patient to maintain normal bathing habits, and are simple to apply. Despite obvious advantages these products are not widely used because of the enormous stinging pain associated with their application to unanesthetized raw surfaces (*British Medical Journal*, 2, July 3, (1954) at page 18.)

It is an object of this invention to prepare a non-stinging wound spray of plastics in a solvent system.

By applying solvents to open wounds produced by sandpaper on the lower arm of 10 subjects it has unexpectedly been discovered that saturated hydrocarbons and chlorofluoro-substituted hydrocarbons are non-stinging solvents. Thus straight or branched chain hydrocarbons containing 5–8 carbon atoms, saturated cyclic hydrocarbons containing 5–8 carbon atoms, and chlorofluoro-substituted saturated hydrocarbons containing 1–2 carbon atoms are non-stinging solvents. Preferred non-stinging solvents are cyclopentane, cyclohexane, cycloheptane, cyclooctane, n-pentane, n-hexane, n-heptane, n-octane, fluorotrichloromethane, sym-tetrachlorodifluoroethane, trifluorotrichloroethane, difluorodichloromethane, difluorochloromethane, and sym-dichlorotetrafluoroethane. The most preferred non-stinging solvent is sym-tetrachlorodifluoroethane.

Common polar solvents such as low molecular weight alcohols, ketones, and esters are determined to be stinging solvents by the above test. Alcohols containing 1–6 carbon atoms, ketones containing 3–7 carbon atoms, and esters of acids containing 1–4 carbon atoms and alcohols having 1–6 carbons are useful solvents for practicing this invention. Methanol, ethanol, n-propyl alcohol, isopropyl alcohol, n-butyl alcohol, isobutyl alcohol, secondary butyl alcohol, ethylene glycol, acetone, methyl ethyl ketone, ethyl acetate, methylamyl acetate, isopropyl acetate, ethyl lactate, chloroform, and trichloroethylene are suitable but not exclusive examples of a stinging polar solvent.

It is often necessary to mix polar stinging solvents with non-stinging solvents to obtain a solvent system with capacity to dissolve a sufficient amount of plastic. It has most surprisingly been found that mixtures of stinging and non-stinging solvents do not themselves have stinging effects. Thus, solvent systems having about 50% stinging solvent and 50% non-stinging solvent do not produce a painful stinging effect when applied to a wound. To be optimally effective it is desirable that the stinging solvent evaporates at a faster rate than the non-stinging solvent; otherwise the concentration of stinging solvent on the wound would exceed the effective concentration as evaporation occurred. Table I lists boiling points of some stinging and non-stinging solvents. These boiling points serve as a guide for relative rates of evaporation.

TABLE I

| Stinging Solvents | | Non-Stinging Solvents | |
|---|---|---|---|
| methanol | 65 | pentane | 36 |
| ethanol | 78 | hexane | 64 |
| acetone | 47 | heptane | 98 |
| ethyl acetate | 77 | octane | 125 |
| methyl ethyl ketone | 79 | cyclopentane | 49 |
| chloroform | 61 | cyclohexane | 81 |
| trichloroethylene | 87 | sym-tetrachlorofluoroethane | 92 |
| | | 1,1,2-trichloro-1,2,2-trifluoroethane | 47 |
| | | 1,1,1,2-tetrachloro-2,2-difluoroethane | 91.5 |

Sym-tetrachlorodifluoroethane is a preferred non-stinging solvent since it evaporates more slowly than most common polar solvents such as ethyl acetate, ethanol, acetone, methanol, and methyl ethyl ketone and has good plastics solvent properties. Table II illustrates the threshold mixture of sym-tetrachlorodifluoroethane and ethanol, acetone, methanol, and methyl ethyl ketone above which pain is not observed upon applying to a wound.

TABLE II

| Mixture of solvents | Mixing relation | Stinging pain |
|---|---|---|
| Sym-tetrachlorodifluoroethane/Ethyl acetate | 60/40 | No |
| | 55/45 | No |
| | 50/50 | No |
| | 45/55 | Yes |
| | 40/60 | Yes |
| Sym-tetrachlorodifluoroethane/Ethanol | 60/40 | No |
| | 55/45 | No |
| | 50/50 | No |
| | 45/55 | Yes |
| | 40/60 | Yes |
| Sym-tetrachlorodifluoroethane/Acetone | 60/40 | No |
| | 55/45 | No |
| | 50/50 | No |
| | 45/55 | Yes |
| | 40/60 | Yes |
| Sym-tetrachlorodifluoroethane/Methanol | 60/40 | No |
| | 55/45 | No |
| | 50/50 | No |
| | 45/55 | Yes |
| | 40/60 | Yes |
| Sym-tetrachlorodifluoroethane/Methyl ethyl ketone | 60/40 | No |
| | 55/45 | No |
| | 50/50 | No |
| | 45/55 | Yes |
| | 40/60 | Yes |

The solvent systems in Table II are particularly advantageous in that they have a high capacity to dissolve a variety of plastic material suitable for wound dressing. Those skilled in the art will recognize that a mixture of several non-stinging solvents or a mixture of several non-stinging and a stinging solvent or several stinging solvents will provide a suitable solvent system. Thus an effective amount of non-stinging solvent is that amount of non-stinging solvent or combination of non-stinging solvents which either alone or in combination with stinging solvent does not cause stinging.

Polymers and copolymers prepared from lower alkyl acrylates and methacrylates having 1 to 3 carbon atoms in the alkyl group such as methyl acrylate, ethyl acrylate, isopropyl acrylate, methyl methacrylate, ethyl methacrylate, propyl methacrylate, methoxyethyl acrylate, ethoxyethyl acrylate, methoxyethyl methacrylate, ethoxyethyl methacrylate, acrylamide, methacrylamide, n-alkyl substituted acrylamides and methacrylamides such as N-methyl, ethyl, propyl acrylamides and methacrylamides, N-vinyl pyrrolidone, hydroxy-(lower alkyl) acrylates and methacrylates form suitable but not exclusive plastic material useful in practicing this invention.

N-butyl methacrylate, isobutyl methacrylate, 2-ethoxyethyl methacrylate and methyl methacrylate form preferable plastics.

Preferred embodiments of plastics in a solvent system, said solvent system containing an effective amount of a non-stinging solvent, are as follows:

| | |
|---|---|
| Sym-tetrachlorodifluoroethane | 25 g. |
| Ethyl acetate | 25 g. |
| 2-Ethoxyethyl methacrylate/methyl methacrylate (90/10 copolymer) | 50 g. |
| Sym-tetrachlorodifluoroethane | 25 g. |
| Acetone | 25 g. |
| n-Butyl/isobutyl methacrylate (50/50 copolymer) | 50 g. |
| Sym-tetrachlorodifluoroethane | 25 g. |
| Ethyl acetate | 20 g. |
| Ethanol | 5 g. |
| n-Butyl/methyl methacrylate (80/20 copolymer) | 30 g. |

Furthermore, medicinally active ingredients such as germicides, fungicides, antibiotics, steroids, local anesthetics or the like may be utilized by having the medicinally active ingredient suspended or entrapped in the polymer, or if desired, dissolved in the liquid phase of the system. Examples of such medicinally active ingredients include 2,4,4'-trichloro-2'-hydroxydiphenyl ether, benzocaine, xylocaine, aspirin, sodium omadine (a derivative of 1-hydroxypyridine-2-thione), hexachlorophene, bacitracin, cortisone, trimethyl benzyl ammonium chloride, cetyl pyridinium chloride, penicillin, Aureomycin (chlorotetracycline), chloromycetin (chloramphenicol), merthiolate, sulfanilamide, sulfathiaozole, sulfaguanidine, sulfapyridine, salicylic acid, Griseofulvin, undecylenic acid, zinc undecylenate, tetracycline, Terracycin (hydroxytetracycline), dienestrol, ethynyl estradiol, diethyl stilbesterol, estradiol, methyltestosterone, progesterone, ascorbic acid. Thus this system of plastic material in a non-stinging solvent is an effective means for topically administering drugs.

The wound dressing of this invention of plastics in a solvent system may be applied by brushing, dabbing, by squeeze bottles or by aerosol spray. Aerosol spray is the preferred method of application, since it provides a thin, tough and transparent film. The invention can be used to form spray-on bandages not only for human wounds but also is useful in the field of veterinary medicine for wounds on the skins of animals such as dogs, cats, sheep, cattle (e.g. to protect cows having mastitis on their teats), goats, pigs and horses and zoological animals such as lions, tigers, deer, zebra, etc. The film can be applied in a matter of seconds; there is no stinging upon application; healing of the wound can be observed; the patient may bath normally, and the film is easily removed after several days. Thus, this invention embodies effective methods of dressing wounds.

Aerosols require that the solvent, plastic and medicinal, if any, be placed in a pressurized container with propellant gases. Suitable propellants include those well known in the art. There can be used compressed gases such as carbon dioxide, nitrous oxide, nitrogen, liquified volatile hydrocarbons such as propane, n-butane, isobutane and 2-methylbutane, methylene chloride, vinyl chloride, fluorinated compounds including perhalogenated compounds and fluorinated hydrocarbons such as dichlorodifluoromethane, 1,1,2-trichloro-1,2,2-trifluoroethane, trichlorofluoromethane, 1,2-dichlorotetrafluoroethane, octofluorocyclobutane, chlorodifluoromethane, 1,1-difluoroethane, vinyl fluoride, vinylidene fluoride, 1-chloro-1,1-difluoroethane. The propellant should contain a substantial amount of volatile material boiling at not over 20°C., but there can also be present a significant amount of less volatile material boiling up to 50°C. Therefore non-stinging aerosol spray wound dressing of propellant gases and plastic material in a solvent system wherein the solvent system has an effective amount of non-stinging solvent, such as sym-tetrachlorodifluoroethane at least 50% when used alone and stinging polar solvent selected from the group comprising alcohols containing 1-6 carbon atoms, ketones containing 1-4 carbon atoms, and esters of acids containing 1-4 carbon atoms and alcohols containing 1-6 carbon atoms or mixtures of the aforementioned polar solvents.

A preferred formulation of a non-stinging aerosol spray wound dressing is:
0.01% Amylacetate
0.47% Ethyl acetate
3.24% 2-Ethoxyethylmethacrylate
0.01% Methylmethacrylate
7.22% Sym-tetrachlorodifluoroethane
26.00% 1,1,2-trichloro-1,2,2-trifluoroethane
29.00% Trifluorochloromethane
24.00% Difluorochloromethane
.003% 2,4,4-Trichloro-2'-hydroxydiphenyl ether.

EXAMPLE 1

A non-stinging wound dressing particularly suited for dabbing or brushing on a wound is prepared by dissolving 50 parts of a 90/10 copolymer of 2-ethoxyethyl methacrylate/methyl methacrylate in a solvent system of 25 parts ethyl acetate and 25 parts sym-tetrachlorodifluoroethane.

EXAMPLE 2

A non-stinging wound dressing particularly suited for dabbing or brushing on a wound is prepared by dissolving 50 parts of a 50/50 copolymer of n-butyl/isobutyl methacrylate in 25 parts sym-tetrachlorodifluoroethane and 25 parts acetone.

EXAMPLE 3

A non-stinging wound dressing particularly suited for dabbing or brushing on a wound is prepared by dissolving 50 parts of a 80/20 copolymer of n-butyl/methyl methacrylate in 25 parts sym-tetrachlorodifluoroethane, 20 parts ethyl acetate, and 5 parts ethanol.

EXAMPLE 4

An aerosol spray container is charged with 200 g. of a formulation which contains
0.01% amylacetate
0.47% ethylacetate
3.24% 2-ethoxyethylmethacrylate
0.01% methylmethacrylate
7.22% sym-tetrachlorodifluoroethane
26.00% 1,1,2-trichloro-1,2,2-trifluoroethane
39.00% trifluorochloromethane
24.00% difluorochloromethane
0.003% 2,4,4'-trichloro-2'-hydroxydiphenyl ether
This formulation provides about 250 spray-on plastic bandages.

EXAMPLE 5

As in Example 4, an aerosol spray formulation without 2,4,4'-trichloro-2'-hydroxydiphenyl ether.

EXAMPLE 6

As in Example 1, a non-stinging wound dressing further containing .001 part of 2,4,4'-trichloro-2'-hydroxydiphenyl ether.

EXAMPLE 7

As in Example 4, an aerosol spray formulation containing 0.003% benzocaine instead of 2,4,4'-trichloro-2'-hydroxydiphenyl ether.

EXAMPLE 8

As in Example 4, an aerosol spray formulation containing 0.003% xylocain instead of 2,4,4'-trichloro-2'-hydroxydiphenyl ether.

EXAMPLE 9

As in Example 4, an aerosol spray formulation containing 0.003% bacitracin instead of 2,4,4'-trichloro-2'-hydroxydiphenyl ether.

EXAMPLE 10

As in Example 4, an aerosol spray formulation containing 0.003% cortisone instead of 2,4,4'-trichloro-2'-hydroxydiphenyl ether.

EXAMPLE 11

As in Example 4, an aerosol spray formulation containing 0.003% chloromphenicol instead of 2,4,4'-trichloro-2'-hydroxydiphenyl ether.

EXAMPLE 12

As in Example 4, an aerosol spray formulation containing 0.003% sulfonilamide instead of 2,4,4'-trichloro-2'-hydroxydiphenyl ether.

EXAMPLE 13

As in Example 4, an aerosol spray formulation containing 0.003% Griseofulvin instead of 2,4,4'-trichloro-2'-hydroxydiphenyl ether.

EXAMPLE 14

As in Example 4, an aerosol spray formulation containing 0.003% zinc undecylenate instead of 2,4,4'-trichloro-2'-hydroxydiphenyl ether.

I claim:

1. In an aerosol wound dressing of the type having in an aerosol spray container pressurized with dichlorodifluoromethane, 1,1,2-trichloro-1,2,2-trifluoroethane, or trichlorofluoromethane which contains a film forming plastic material selected from the group consisting of N-butyl methacrylate, isobutyl methacrylate, 2-ethoxyethyl methacrylate, methyl methacrylate, 2-ethoxyethyl methacrylate/methyl methacrylate(90/10 copolymer), N-butyl methacrylate/isobutyl methacrylate(50/50 copolymer), or N-butyl methacrylate/methyl methacrylate(80/20 copolymer) in a solvent system, the improvement which comprises a solvent system having sym-tetrachlorodifluoroethane alone or at least 50% sym-tetrachlorodifluoroethane in combination with methanol, ethanol, acetone, methyl ethyl ketone, ethyl acetate, or amyl acetate; said improvement rendering the aerosol wound dressing non-stinging.

2. As in claim 1, a non-stinging aerosol spray wound dressing comprising:
    0.1% amylacetate
    0.47% ethylacetate
    3.24% 2-ethoxyethylmethacrylate
    0.01% methylmethacrylate
    7.22% sym-tetrachlorodifluoroethane
    26.00% 1,1,2-trichloro-1,2,2-trifluoroethane
    39.00% trifluorochloromethane
    24.00% difluorochloromethane
in an aerosol spray container.

3. As in claim 1, a non-stinging aerosol spray wound dressing further comprising .003% 2,4,4'-trichloro-2'-hydroxydiphenyl ether.

* * * * *